United States Patent
Doll et al.

(10) Patent No.: US 8,822,712 B1
(45) Date of Patent: Sep. 2, 2014

(54) PROCESS TO PREPARE A PHOSPHOROUS CONTAINING VEGETABLE OIL BASED LUBRICANT ADDITIVE

(75) Inventors: Kenneth M. Doll, Peoria, IL (US);
Brajendra K. Sharma, Savoy, IL (US);
Paulo A. Suarez, Brasilia (BR)

(73) Assignees: The United States of America, as represented by the Secretary of Agriculture, Washington, DC (US); The Penn State Research Foundation, University Park, PA (US)

( * ) Notice: Subject to any disclaimer, the term of this patent is extended or adjusted under 35 U.S.C. 154(b) by 349 days.

(21) Appl. No.: 13/220,788

(22) Filed: Aug. 30, 2011

Related U.S. Application Data

(60) Provisional application No. 61/379,163, filed on Sep. 1, 2010.

(51) Int. Cl.
*C07F 9/02* (2006.01)
*C07F 9/6571* (2006.01)

(52) U.S. Cl.
CPC .................. *C07F 9/02* (2013.01)
USPC ............... 554/79; 508/422; 508/224; 554/78; 554/124

(58) Field of Classification Search
None
See application file for complete search history.

(56) References Cited

U.S. PATENT DOCUMENTS

| | | | | |
|---|---|---|---|---|
| 2,490,748 A | * | 12/1949 | Dickey | 554/78 |
| 2,965,657 A | * | 12/1960 | Findley | 554/79 |
| 5,221,796 A | * | 6/1993 | Mori et al. | 554/79 |
| 5,552,070 A | * | 9/1996 | Schafer et al. | 508/224 |
| 6,734,315 B1 | * | 5/2004 | Nowak et al. | 549/527 |
| 2008/0103073 A1 | * | 5/2008 | Adhvaryu | 508/426 |

OTHER PUBLICATIONS

Kirk-Othmer, Encyclopedia of Chemical Technology, 4th edition, 1993, John Wiley & Sons, vol. 10, pp. 267 (3 pages).*
Burg, D.A. et al., Meadowfoam fatty amides: preparton, purification, and use in enrichment of 5,13-docosadienoic acid and 5-eicosenoic acid, 1991, JAOCS, vol. 68, No. 3, pp. 190-192.*

(Continued)

*Primary Examiner* — Yate K Cutliff
(74) *Attorney, Agent, or Firm* — John D. Fado; G. Byron Stover; Gail E. Poulos

(57) ABSTRACT

Chemically-modified triglycerides are prepared by reacting epoxidized triglyceride oils with phosphorus-based acid hydroxide or esters. The phosphorus-containing triglyceride derivatives are of the formula:

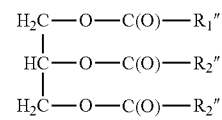

wherein $R_1''$, $R_2''$ and $R_3''$ are independently selected from C3 to C29 aliphatic fatty acid residues, at least one of which comprising one or both of the derivatized methylene groups of the formula:

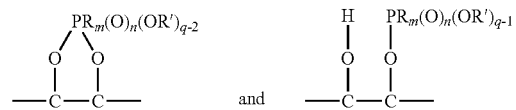

wherein m is 0, 1 or 2, n is 0 or 1, q is 1, 2 or 3, and R and R' are independently selected from the group consisting of H, straight, branched or cyclic hydrocarbons and substituted hydrocarbons, and aryl groups. The phosphorus-containing triglyceride derivatives so produced have utility as antiwear/antifriction additives for industrial oils and automotive applications.

36 Claims, 2 Drawing Sheets

(56) References Cited

OTHER PUBLICATIONS

Cahoon, E.B., et al., Production of fatty acid components of Meadowfoam oil in Somatic Soybean Embryos, 2000, Plant Physiologists, vol. 124, pp. 243-251.*

Moser, B.R., et al., Biodiesel form meadow foam (*Limnanthes alba* L.) seed oil: oxidative stability and unusual fatty acid composition, Jan. 2010, Enerty & Environmental Science, vol. 3, pp. 318-327 (11 pages with cover).*

Placek, L. L., et al., A review on Petroselinic acid and its derivatives, 1963, JAOCS, vol. 40, pp. 319-329.*

Derouet, Daniel, et al., "Chemical modification of 1,4-polydienes by di(alkyl or aryl)phosphates", European Polymer Journal, 37, 2001, pp. 1297-1313.

Guo, Yinzhong, et al., "Hydrolysis of Epoxidized Soybean Oil in the Presence of Phosphoric Acid", J Am Oil Chem Soc, 2007, 84, pp. 929-935.

Maffei, Michel, et al., "A two step synthesis of 2-oxo-2-vinyl 1,3,2-dioxaphospholanes and -dioxaphosphorinanes", Tetradedron, 59, 2003, pp. 8821-8825.

* cited by examiner

PROCESS TO PREPARE A PHOSPHOROUS CONTAINING VEGETABLE OIL BASED LUBRICANT ADDITIVE

CROSS-REFERENCE TO RELATED APPLICATIONS

This application claims the benefit under 35 U.S.C. 1.19(e) of U.S. provisional 61/379,163 filed Sep. 1, 2010, the contents of which are incorporated by reference herein.

BACKGROUND OF THE INVENTION

1. Field of the Invention

The invention relates to novel phosphorous-containing triglyceride derivatives and a process for their preparation.

2. Description of the Prior Art

Antiwear/antifriction lubricants typically comprise a base oil that has been blended with any number of additives that enhance the ability of the base oil to withstand the mechanical stresses of interacting working surfaces under boundary lubrication conditions. Most of the lubricants and many of the additives currently in daily use originate from petroleum base stocks that are toxic to environment, making it increasingly difficult for safe and easy disposal. There has been an increasing demand for "green" lubricants [Rhee, I., NLGI Spokesman, 60 (5):28 (1996)] and lubricant additives in recent years due to concerns about loss of mineral oil-based lubricants to the environment and increasingly strict government regulations controlling their use.

Vegetable oils are readily biodegradable, safe to handle, environmentally friendly, non toxic fluids that are also readily renewable resources [Salunkhe, D. K. et al., World Oil Seed Chemistry, Technology and Utilization, Van Nostrand Reinhold, New York, (1992) pp. 1-8; Bockish, M. (ed.) Fats and Oils Handbook, AOCS Press, Champaign, (1998) 838]. The triacylglycerol structure of vegetable oil, which is also amphiphilic in character, give it an excellent potential as a candidate for use as a lubricant or functional fluid [Zaher, F. A. et al., Vegetable oils and lubricants, Grasas Aceites (Seville), 39:235-238 (1988); Willing, A., Chemosphere, 43:89-98 (2001)]. Triacylglycerol molecules orient themselves with the polar end at the solid surface making a close packed monomolecular [Brockway, L. O., J. Colloid Sci., 2:277-289 (1947)] or multimolecular layer [Fuks, G. I., Research in surface forces, A. B. V. Deryagin (ed.) Consultants Bureau, New York (1963) 29-88] resulting in a surface film on the material being lubricated. In addition, the vegetable oil structure provides sites for additional functionalization, offering opportunities for improving on the existing technical properties such as thermo-oxidative, low temperature stability and lubricity. These properties make them very attractive for industrial applications that have potential for environmental contact through accidental leakage, dripping, or generation of large quantities of after-use waste materials requiring costly disposal [Randles, S. J., et al., J. Syn. Lubr., 9:145-161 (1992); Dick, R. M., Process, 41:339-365 (1994)].

Limitations on the use of vegetable oil in its natural form as an industrial base fluid or as an additive relate to poor thermal/oxidation stability [Becker, R., et al., Lubr. Sc., 8:95-117 (1996); Adhvaryu, A., et al., Thermochimica Acta, 364 (1-2): 87-97 (2000) and ref. within], poor low temperature behavior [Asadauskas, S., et al., J. Am. Oil Chem. Soc., 76: 313-316 (1999); Adhvaryu, A., et al., Thermochimica Acta, 395:191-200 (2003) and ref. within], and other tribochemical degrading processes [Brophy, J. E. et al., Ann N.Y. Academy Sci., 53:836-861 (1951); Miller, A. et al., Lubr. Eng., 13:553-556 (1957)] that occur under severe conditions of temperature, pressure, shear stress, metal surface and environment. To meet the increasing demands for stability during various tribochemical processes, the oil structure has to withstand extremes of temperature variations, shear degradation and maintain excellent boundary lubricating properties through strong physical and chemical adsorption with the metal. The film-forming properties of triacylglycerol molecules are believed to inhibit metal-to-metal contact and progression of pits and asperities on the metal surface. Strength of the protective fluid film and extent of adsorption on the metal surface dictate the efficiency of a lubricant's performance. It has also been observed that friction coefficient and wear rate are dependent on the adsorption energy of the lubricant [Kingsbury, E. P., ASLE Trans., 3:30-33 (1960)].

The antiwear properties of commercial additives are derived from a variety of elements capable of reacting with the metal surface and establish a stable protective film. Phosphorus, sulfur, nitrogen and zinc constitute the active element in most mineral oil based commercial antiwear additives.

SUMMARY OF THE INVENTION

By virtue of this invention, we now provide a novel class of chemically-modified triglycerides prepared by reacting epoxidized triglyceride oils or alkyl esters thereof with phosphorus-based acid hydroxide or esters. In the process, an epoxidized triglyceride comprising at least one epoxidized fatty acid which has one or more oxirane rings of the formula:

(1)

is reacted with a phosphorus-based acid hydroxide or ester of the formula $R_m P(O)_n$—$(OR')_q$, wherein m is 0, n is 0 or 1, q is 1, 2 or 3, and R and R' are independently selected from the group consisting of H, straight, branched or cyclic hydrocarbons and substituted hydrocarbons, and aryl groups; wherein if one R' is H then at least one of the other R' is not H. In the reaction, the oxirane ring is opened and forms either or both of the derivatized methylene groups of the formula:

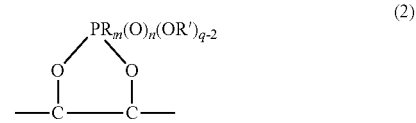

(2)

and

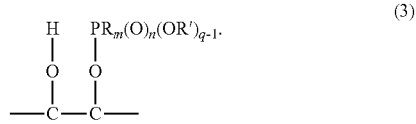

(3)

The resultant phosphorus-containing triglyceride derivatives of this invention are of the formula:

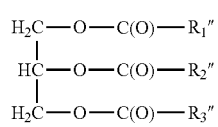

(4)

wherein $R_1''$, $R_2''$ and $R_3''$ are independently selected from C3 to C29 aliphatic fatty acid residues, at least one of which comprising one or both of the above-mentioned derivatized methylene groups of formulas (2) and (3). The phosphorus-containing triglyceride derivatives so produced have utility as antiwear/antifriction additives for industrial oils and automotive applications.

In accordance with this discovery, it is an object of this invention to provide novel vegetable oil derivatives.

It is also an object of the invention to provide environmentally-friendly triglyceride oil-based industrial fluids having acceptable antiwear/antifriction performance properties.

Another object of the invention is to introduce a new use for triglyceride oils and to expand the market for an agricultural commodity.

A further object of the invention is to produce industrial fluids that reduce the demand on petroleum resources and that are biodegradable.

It is another object of the invention to provide a synthetic route for converting epoxidized sites of unsaturation in triglyceride fatty esters to a phosphorus functionality.

Other objects and advantages of this invention will become readily apparent from the ensuing description.

DETAILED DESCRIPTION

Figure 1:
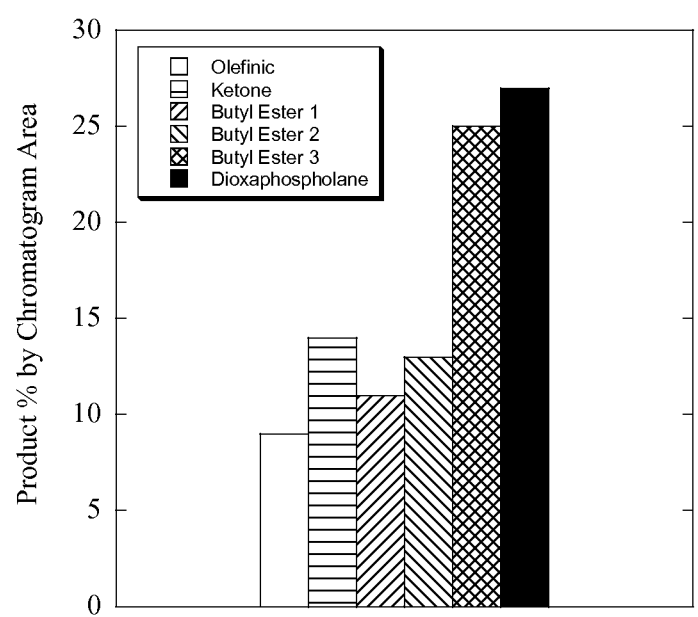
FIG. 1 shows the distribution of the major products, shown in scheme 2 in Example 1, from the reaction of EMO with dibutyl phosphate at 120° C. for 72 hours.

Using the process of this invention, phosphorus-containing triglyceride derivatives may be formed from triglycerides composed of fatty acid ester groups that collectively comprise at least one epoxide moiety. These epoxides may be produced from a variety of unsaturated vegetable oils, animal fats as described below, or they may be obtained from commercial sources. When preparing the epoxides, the starting triglyceride is not critical, and any triglyceride having a $\Delta^3$ to $\Delta^{17}$ unsaturated fatty acid (i.e. having a double bond between $\Delta^3$ and $\Delta^{17}$ inclusive) containing from 4 to 30 carbon atoms or longer may be used. The generic chemical structure of triglyceride oils for use in preparing the epoxidized triglycerides is represented by the formula, below:

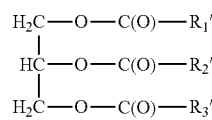

(5)

wherein $R_1'$, $R_2'$ and $R_3'$ are independently selected from C3 to C29 aliphatic fatty acid residues, that may be completely saturated or have sites of unsaturation and/or hydroxylation, provided that $R_1'$, $R_2'$ and $R_3'$ collectively have at least 1 but preferably more sites of unsaturation. In most of the common triglyceride oils listed above, the triglyceride esters are composed of C18 and C16 fatty acids, and accordingly $R_1'$, $R_2'$ and $R_3'$ are C17 or C15.

Triglycerides composed of unsaturated fatty acids are naturally occurring in a variety of plant oils or animal fats and may be conveniently obtained for use therefrom. Without being limited thereto, oils which may be used as sources include soybean, cottonseed, corn, olive, peanut, palm, sesame, sunflower, canola, castor, safflower, linseed, grapeseed, oiticia, tung, rice, crambe, high erucic rape, algae oils, animal fat, and high oleic canola oils, with soybean oil being particularly preferred.

In a preferred embodiment, the triglyceride oils principally contemplated herein include what are normally referred to as the triglyceride drying oils. The vegetable triglyceride drying oils include plant oils and plant source-like synthetic and semi-synthetic triglycerides that can be transformed into hard, resinous materials [see Encyclopedia of Polymer Science and Technology, H. F. Monk et al., eds., John Wiley & Sons, (1966), pp. 216-234]. The expression "drying oils" is generic to both true drying oils, which dry (harden) at normal atmospheric conditions, and semidrying oils, which must be baked at elevated temperatures in order to harden. Unless otherwise indicated, "drying oil" will be used herein in its broadest sense to refer to both types of drying oil. The unsaturated fatty acids (e.g., linoleic or linolenic) residues of a drying or semidrying oil comprise double bonds that are readily available for entering into an oxidative reaction, or other reactions involved in the drying process. These oils may also include oleic fatty acid residues. Common sources of drying oils include cottonseed oil, castor oil, canola oil, linseed oil, oiticica oil, safflower oil, soybean oil, sunflower oil, corn oil, and tung oil. Of these oils, soybean oil is most readily available in both its unmodified and epoxidized state, and is therefore the most preferred. The properties of the subject industrial lubricants can be tailored by blending together different drying oils, or by blending drying oils with non-drying oils. Non-drying oils substantially comprise saturated and/or monounsaturated fatty acid residues, such as those characteristic of palmitic, stearic and oleic acid. Exemplary nondrying oils include palm, peanut, olive, and grapeseed oils.

Because of ready availability and low cost, the preferred vegetable oil use herein is soybean oil. The fatty acid constituents of soybean oil are mainly oleic (18:1), linoleic (18:2) and linolenic (18:3) acids. Though the relative distribution of fatty acids is largely dependent on the soybean type and its genetic makeup, soybean oil typically consists of approximately $C_{16}$=4%, $C_{18}$=3%, $C_{18:1}$=22%, $C_{18:2}$=66% and $C_{18:3}$=5%.

The practitioner skilled in the art will of course recognize that for products requiring a high degree of purity or uniformity, the oils may first be hydrolyzed to obtain free fatty acids for use as starting materials in the reaction. Hydrolysis of the oils to the fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: Official and Tentative Methods of the American Oil Chemist's Society, third edition, AOCS, Chicago, Ill., (1973)]. Other conventional techniques including splitting with steam under pressure are also effective.

Once the starting material has been selected, the triglycerides composed of the unsaturated fatty acids are reacted under conditions and for a period of time effective to at least partially, but preferably completely, epoxidize the carbon/carbon double bonds therein. These epoxidized triglycerides will contain one or more oxirane rings (which may also be referred to as epoxidized methylene groups):

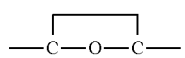
(1)

or the equivalent formula:

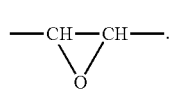
(6)

A variety of techniques for the epoxidation of olefins are known in the art and are suitable for use herein. For example, without being limited thereto, suitable techniques include those described by Qureshi et al. (Polymer Science and Technology, Vol. 17, Plenum Press, p. 250), Croco et al. (U.S. Pat. No. 5,166,372), Nowak et al. (U.S. Pat. No. 6,740,763 or 6,734,315), and preferably Bunker and Wool (Synthesis and characterization of monomers and polymers for adhesives from methyl oleate. J. Polym. Sci., Part A: Polym. Chem. 2002, 40, 451-458), the contents of each of which are incorporated by reference herein. In accordance with the preferred embodiment, epoxidation is effected by reaction of the unsaturated triglyceride with a combination of a peroxide and a carboxylic acid or its anhydride, or by reaction with a peroxycarboxylic acid such as peroxy-benzoic acid. Suitable peroxides include hydrogen peroxide or any organic peroxides which will form a peracid with a carboxylic acid or its anhydride. However, preferred epoxidation reagents include hydrogen peroxide with either formic acid, benzoic acid, acetic acid, or acetic anhydride. The order of addition is not critical, and the peroxide and carboxylic acid may be combined prior reacting with the triglyceride, or they may be added separately to the triglyceride, or all of the peroxide, carboxylic acid, and triglyceride may be combined concurrently. The reaction is preferably conducted at low temperatures, more preferably between about 0 and about 30° C., most preferably between about 0 and about 25° C. Because the reaction is exothermic, the temperature is preferably controlled such as by cooling. In a particularly preferred embodiment reaction is initiated at a temperature of approximately 0° C. and maintained at this temperature for about 1 hour, before the temperature is allowed to increase to room temperature. The reaction is typically completed in approximately 3 to 6 hours.

As an alternative to producing the epoxidized triglycerides, it is understood that many of these same epoxidized triglycerides may be obtained in pure form or as mixtures from commercial sources. In this embodiment, the epoxidation reaction is thereby unnecessary and the invention may proceed directly with the phosphorus reaction described herein. The final products will of course be the same.

In accordance with the process of this invention, the epoxidized triglyceride produced or otherwise obtained as described above is reacted with a phosphorus-based acid hydroxide or ester to open the oxirane ring and form derivatized methylene groups of either or both of two predominant forms as described below, depending upon the particular phosphorus-based acid hydroxide or ester used and the conformation of the epoxide. A variety of phosphorus-based acid hydroxide or ester reactants are suitable for use herein and may be represented by the formula $R_m P(O)_n\text{---}(OR')_q$ wherein m is 0, 1 or 2, n is 0 or 1, q is 1, 2 or 3, and R and R' are independently selected from the group consisting of H, straight, branched or cyclic hydrocarbons, substituted straight, branched or cyclic hydrocarbons, and aryl groups. However, in a preferred embodiment, at least one R' is H. The length of the hydrocarbons is not critical, and may be as small as 3 carbons, with C3 to C40 hydrocarbons being preferred and C6 to C22 hydrocarbons being more preferred. The cyclic hydrocarbon may be saturated or unsaturated, substituted or unsubstituted, as well as heterocyclic. Without being limited thereto, preferred phosphorus-based acid hydroxide or ester include phosphates (i.e., m=0, n=1 and q=3), phosphonates (i.e., m=1, n=1 and q=2), phosphinates (i.e., m=2, n=1 and q=1), and phosphite esters (i.e., m=0, n=0 and q=3), with phosphates being particularly preferred.

The reaction is optionally conducted in the presence of a effective amount of a catalyst. Suitable catalysts should be capable of opening the oxirane ring of the epoxide, and a variety of catalysts may be used, including mineral acids, Lewis acids, acidic resins, and enzymes, with ionic liquids, mineral acids or Lewis acids being preferred. By way of example and without being limited thereto, suitable catalysts include $H_2SO_4$, $H_3PO_4$, $BF_3$ etherate, $CeCl_3$, $ZnCl_2$, $InCl_3$, $SbCl_3$, $AlCl_3$, $Zn(ClO_4)_2$, $Cu(ClO_4)_2$, and choline chloride/urea, acidic resins such as AMBERLYST-15 (Rohm Haas), solid catalysts, such as mixed metal oxides, and enzymes such as lipases. The amount of the catalyst may vary somewhat with the particular catalyst selected, although even very small amounts are effective. Without being limited thereto, typically the catalyst will be added at a concentration of about 0.5% or higher (measured by weight of the reaction mixture), preferably at a concentration of about 1 to 10%, and most preferably at a concentration of about 5%. The use of a solvent is also optional, as the reaction may be conducted neat, without the addition of solvent. However, if the triglyceride and phosphorus-based acid hydroxide or ester are not sufficiently miscible, an organic solvent such as heptane, hexane or other hydrocarbon, or acetone may be used. The reaction temperature is not critical, and the reaction is typically conducted at a temperature below about 150° C., preferably between about 70 to 120° C. Reaction time may vary with temperature and catalyst concentration, and the reaction typically reaches completion in less than about 2 hours at 120° C. with 5% catalyst by weight, and about 8-24 hours at 95° C., although some side reactions continue to occur for up to 72 hours. At the completion of the reaction, any ionic liquid or solid catalyst may be recovered and recycled.

The reaction of the epoxidized triglyceride with phosphorus-based acid hydroxide or ester reactants, occurs in a single step, with the oxirane ring opening of the triglyceride and forming one or both of two derivatized methylene groups of the formulas:

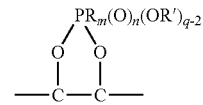
(2)

and

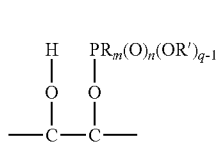
(3)

wherein m, n, q, R and R' are as described above. For reactions using phosphorus-based acid hydroxide or ester reactants having two or three hydroxyl or ester moieties (i.e., q is 2 or 3), a mixture of these two derivatives are formed, with the cyclic derivative of formula (2) being predominant, >90%. Conversely, for reactions using phosphorus-based acid hydroxide or ester reactants having a single hydroxyl or ester moiety (i.e., q is 1), only the hydroxyl derivative of formula (3) is formed. Reactions using epoxidized triglycerides wherein the epoxide moieties are in the cis-conformation also greatly favor the production of the cyclic derivative of formula (2), while reactions using epoxidized triglycerides wherein the epoxide moieties are in the trans-conformation also favor the production of the hydroxyl derivative of formula (3).

The resultant triglyceride derivatives may be characterized by formula:

$$H_2C-O-C(O)-R_1''$$
$$HC-O-C(O)-R_2''$$
$$H_2C-O-C(O)-R_3''$$
(4)

wherein $R_2''$, $R_2''$ and $R_3''$ are independently selected from C3 to C29 aliphatic fatty acid residues comprising one or more of the derivatized methylene groups:

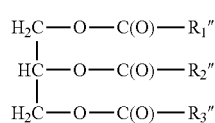
(2)

and

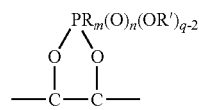
(3)

wherein m, n, q, R and R' are as described above.

Following completion of the reaction, the phosphorous-containing triglyceride derivatives comprising the different above-mentioned derivatized methylene groups may be separated from one another (as well as any other by-products) and recovered in pure or substantially pure form (approximately 85% purity or greater) A variety of techniques are suitable for separation of the derivatives, although high performance liquid chromatography is preferred on a small scale and preparative liquid chromatography for large scale.

The phosphorous-containing triglyceride derivatives of this invention have superior properties which render them useful as additives to base stocks for biodegradable lubricant applications, such as crankcase oils, transmission fluids, two-cycle engine oils, marine engine oils, greases, hydraulic fluids, drilling fluids, metal cutting oils, and the like. Base stocks useful in the lubricant formulations contemplated by the invention are typically high molecular weight hydrocarbons, and may be of mineral, vegetable, or synthetic origin, or mixtures thereof. Exemplary base oils are described in Erickson et al. (U.S. Pat. No. 5,023,312, the contents of which are incorporated herein by reference). Of course, the objectives of the invention to maximize the biodegradability of the lubricant system would be achieved with a vegetable oil base stock.

Though formulations of base stocks with the phosphorous-containing triglyceride derivatives of the invention meet or exceed many, if not all, specifications for lubricant end-use applications, it is contemplated that other additives may be used in conjunction with the phosphorus containing triglyceride derivatives in order to enhance the properties of the base stock. Illustrative of these additives are detergents, antiwear agents, antioxidants, viscosity index adjusters, pour point depressants, corrosion protectors, friction coefficient modifiers, colorants and the like as well-known in the art.

The amount of phosphorous-containing triglyceride derivatives additive formulated with a base oil will of course depend upon the end-use application of the formulation. For most of the end-uses indicated above, the concentration of additive will be in the range of about 1-12% (w/w), typically at least about 4% (w/w), and preferably in the range of about 5-8% (w/w).

The following examples are intended only to further illustrate the invention and are not intended to limit the scope of the invention as defined by the claims.

Example 1

Materials and Methods

Materials

Methyl oleate (Sigma-Aldrich, St. Louis, Mo., Tech 70%), hydrogen peroxide (Sigma-Aldrich, St. Louis, Mo., A.C.S. Reagent, 30% Solution), formic acid (Sigma-Aldrich, 96%, A.C.S. reagent), heptane (EMD, Gibbstown N.J., Omnisolve), sodium chloride, (Fisher, Fairlawn, N.J., A.C.S. Reagent), sodium bicarbonate (Fisher, Fairlawn, N.J., A.C.S. Reagent), sodium hydroxide (Fisher, Fairlawn, N.J., A.C.S. Reagent), acetonitrile (Fisher, Fairlawn, N.J., HPLC grade), butanol (Fisher, Fairlawn, N.J., A.C.S. Reagent), Titanium (IV) butoxide (Sigma-Aldrich, St. Louis, Mo., 97%), Zirconium (IV) butoxide (Sigma-Aldrich, St. Louis, Mo., 80%), dibutyl phosphate (Sigma-Aldrich, St. Louis, Mo., 97%), bis-2-ethylhexyl phosphate (Sigma-Aldrich, St. Louis, Mo., 97%), diphenyl phosphate (Sigma-Aldrich, St. Louis, Mo., 99%) were used as received.

Synthesis of Titanium/Zirconium Catalyst

The catalyst employed in one of the reactions reported herein was made according to a method soon to be in the literature (Pereira et al., 2010. Characterization of single ZrO2 and TiO2 oxides and mixed ZrO2-TiO2 oxides used as catalysts. Manuscript in progress). Titanium (IV) butoxide and Zirconium (IV) butoxide were dissolved in butanol in desired molar ratios, ~25 g total oxide in 20 mL of butanol, and stirred for 20 minutes. Next, 50 mL of deionized water was added and a precipitate was formed. Precipitation was allowed to continue for 4 hours and then the solutions were filtered and the precipitates were dried at 150° C. for 96 hours. The catalysts were then calcined at 400° C. for 8 hours, then cooled under nitrogen.

Gas Chromatography

The gas chromatograph-mass spectrometer (GC-MS) employed was an Agilent (Santa Clara, Calif.) 7890A gas chromatograph equipped with a 7683B series injector and a 5975 C mass detector. A Windows XP equipped HP-Compaq DC7700 computer with a 3.39 GHz Pentium D processor and using Agilent MSD Enhanced Chemstation Version E01.00.237 controlled the instrument and acquired and processed data. The GC column employed was an HP-5MS (Agilent, Santa Clara, Calif.), 30 m×0.25 mm with film thickness 0.25 um. A helium flow rate of ~0.8 mL min$^{-1}$, an injection volume of 0.1 μL and a 50:1 split ratio were all used. The temperatures were as follows: Inlet 220° C., Detector 220° C., Auxiliary transfer line 250° C., MSD 150° C. The initial temperature of 150° C. was held for 2 min and then ramped to 280° C. at 15° C. min$^{-1}$ where it was held for 20 min. The detector was ran in the EI mode and set to scan for m/z ratios from 50 to 500 Daltons.

NMR

NMR was performed on a Bruker (Boston, Mass.) Avance 500 NMR spectrometer operating at 500 MHz for $^1$H, 125 MHz for $^{13}$C, and 202 MHz for $^{31}$P. Bruker Icon NMR software was used on a HP×1100 Pentium 4 workstation. Peaks in the $^1$H and $^{13}$C spectra were referenced to tetramethyl silane 0.00 ppm and to phosphoric acid in the $^{31}$P experiments. Simulations of $^{13}$C NMR spectra were performed by ACD/Labs 6.00 ACD/CNMR predictor software, running on a Gateway Pentium 4 CPU with a 2.53 GHz processor, or on ChemDraw Ultra 11, version 11.0.1, running on a Windows XP Dell Optiplex 760 with an Intel Core 2 Duo 2.99 GHz processer.

Synthesis of Epoxidized Methyl Oleate (EMO)

EMO was synthesized according to prior literature methods (Bunker and Wool, 2002. Synthesis and characterization of monomers and polymers for adhesives from methyl oleate. J. Polym. Sci., Part A: Polym. Chem. 40, 451-458; Doll and Erhan, 2005. Synthesis of carbonated fatty methyl esters using supercritical carbon dioxide. J. Agric. Food Chem. 53, 9608-9614; Findley et al., 1945. Epoxidation of Unsaturated Fatty Materials with Peracetic Acid in Glacial Acetic Acid Solution. J. Am. Chem. Soc. 67, 412-414; Schmits and Wallace, 1954. Epoxidation of Methyl Oleate with Hydrogen Peroxide. J. Amer. Oil Chem. Soc. 31, 363-365). In short, methyl oleate was placed into a roundbottom flask and 4 equivalents of formic acid was added. The reaction was cooled in an ice bath, and 2 equivalents of 30% hydrogen peroxide solution was added dropwise over about 5 minutes with continuous stirring of the solution. The ice bath was removed and the reaction allowed to proceed. The temperature was monitored and the reaction was not allowed to get above 30° C. Reaction progress was monitored by taking aliquots, dissolving in heptane and injecting into the GC-MS. After the reaction was done, ~1 volume of heptane was added to help layer the solution with and a separatory funnel was used to remove the acid/peroxide layer. Sodium bicarbonate solution was added, shaken with the product layer, then removed. This was repeated until the solution was no longer acidic as measured by pH paper. A saturated sodium chloride solution was shaken with the product layer, removed, and the product was dried by rotary evaporation and then on a short path drying apparatus.

Synthesis of Phosphorous Containing Compounds

In a small dried reaction vial, 625 mg of EMO was added to 650 mg bis-2-ethylhexyl phosphate or 450 mg of dibutyl phosphate. Separate reactions were conducted with and without catalyst. In the reactions where catalyst was used, it was added at this time. The reaction was capped and a conical magnetic stirbar matched to the reaction vial was used. The reaction was heated to the reaction temperature, 95, 120, or 140° C., and the reaction allowed to proceed for 24-72 hours. The reaction was filtered using a syringe filter and further analysis was performed. Reactions of twice this scale were also performed.

Analysis of Reaction Samples

The analysis of the reaction solutions were performed by taking ~20 μL of sample, diluting into 1 mL heptane. These solutions were injected into the GC-MS as described above. The areas of the total ion count chromatographs (TIC) were used to determine the extent of the reaction.

The identification of the products was done by their mass spectra. Additionally, the NMR was taken on the dioxaphospholane compound purified by the HPLC-MS method, detailed in section 2.3.2. The $^1$H NMR was not assigned due to the number of signals. The $^{13}$C NMR: (125 MHz, CDCl$_3$ from TMS) δ 174 (cabonyl carbon), δ 84, (carbons in dioxophospholane), δ 51 (methoxy carbon), δ 64 (first carbon of butyl chain phosphate), δ 14 (2 signals, end carbon of fatty chain and phosphate butyl chain), δ 20-35 (multiple signals) were all as expected from simulation. A small amount of ketone was also identified in this purified product by NMR signals at δ 211 (ketone carbon) and δ 43 (carbon next to ketone). The $^{31}$P NMR (202 MHz, CDCl$_3$ from phosphoric acid) δ 18.19 and δ 18.14 correspond to the 2 stereoisomer of dioxaphospholane.

Separation of Products

On the material from one of the larger scale reactions, separation was accomplished by preparative liquid chromatography. A 1 g sample of the mixed product was dissolved in 5 mL of acetonitrile, and then injected into the chromatograph using a standard injection valve and loop. The column used was a 375 mm×16 mm column of C18 gel. The eluent was 100% acetonitrile fed at 1 mL/min. Elution was monitored using refractive index detector on a chart recorder. Fractions were collected and the solvent was removed by rotary evaporation yielding materials which were analyzed by gas chromatography-mass spectrometry.

Results and Discussion

The reactions of EMO with various alkyl and aryl phosphates, including dibutyl phosphate, are shown in the following Schemes 1 and 2. The reaction shown in scheme 2 was conducted at 120° C. for 72 hr.

Scheme 1:

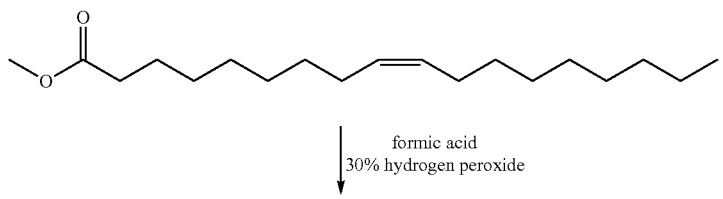

11      12
-continued
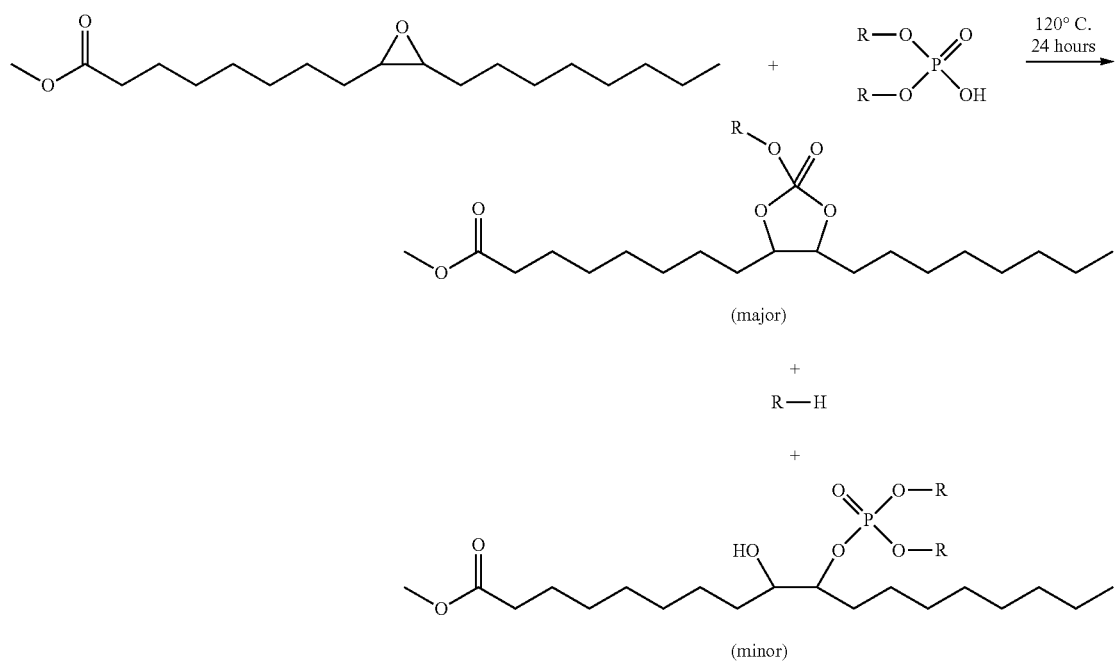
Scheme 2:
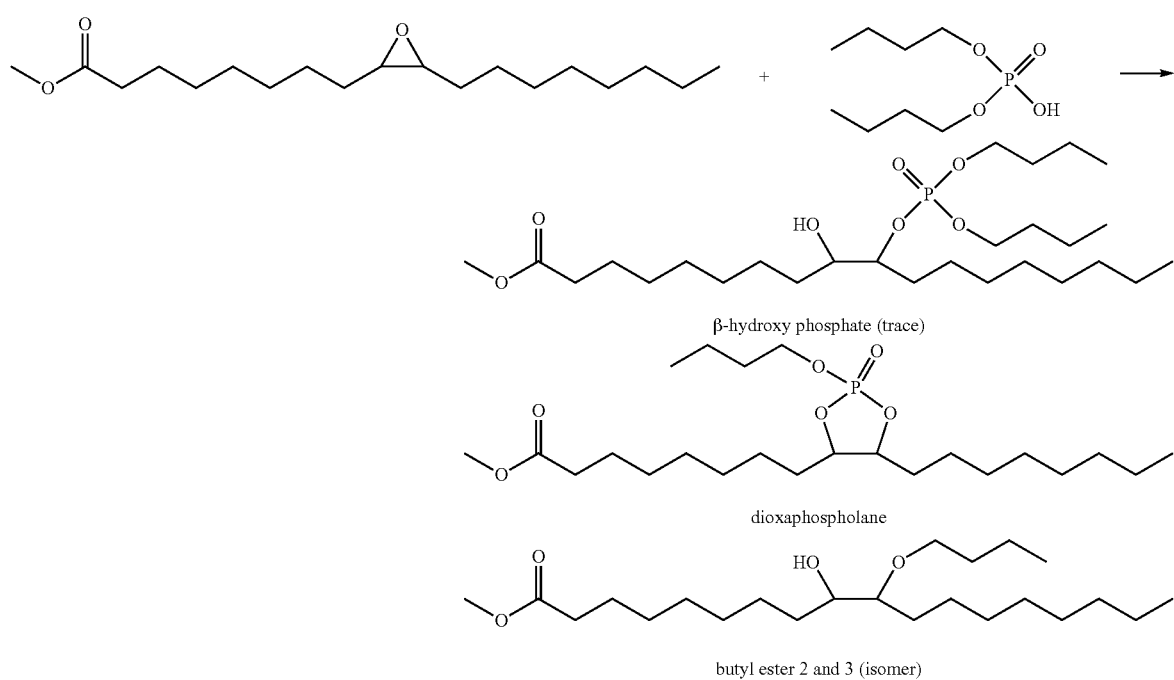

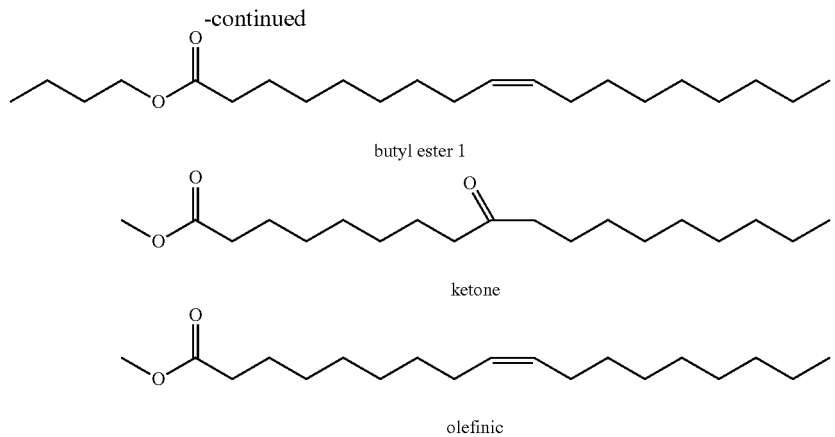

butyl ester 1 ketone olefinic

Figure 2:
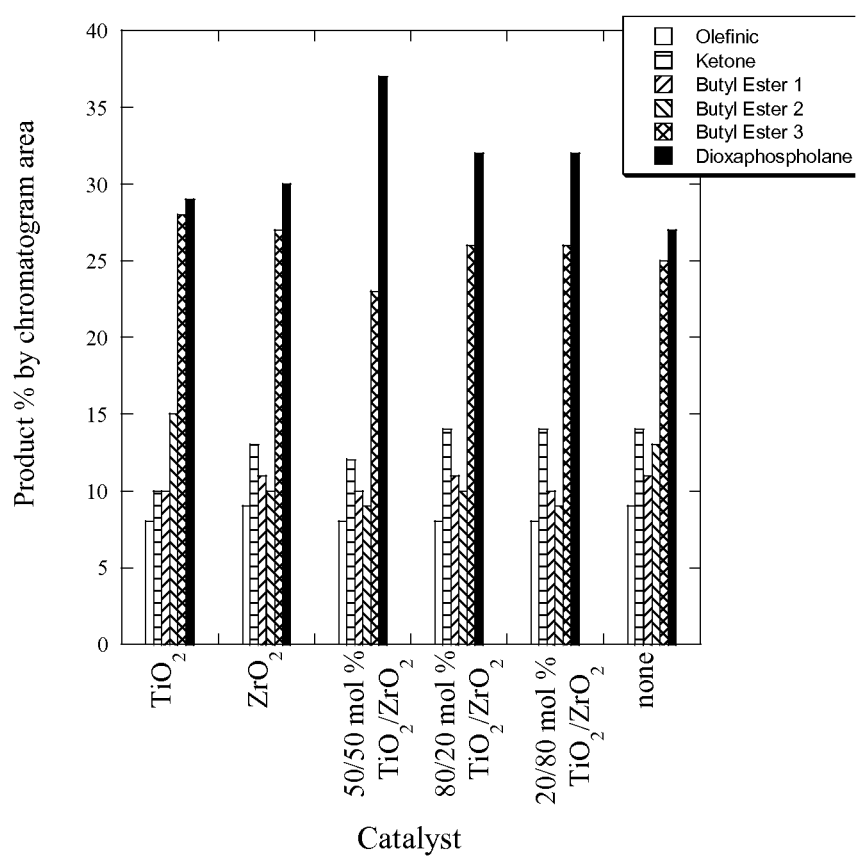
FIG. 2 shows the reaction product distributions, shown in scheme 2 in Example 1, of the reaction of EMO with dibutyl phosphate at 120° C. for 72 hours with various titanium and zirconium oxide catalysts.

The products in scheme 2 were tentatively identified by mass spectrometry. The addition of catalyst did not affect the reaction products and did not significantly affect the distribution of the products. The distribution of the major products in reaction scheme 2 without catalyst is shown in FIG. 1, while the distribution of the major products in reaction scheme 2 with various added catalysts is shown in FIG. 2.

It is understood that the foregoing detailed description is given merely by way of illustration and that modifications and variations may be made therein without departing from the spirit and scope of the invention.

We claim:

1. A method of making cyclic phosphorous-containing triglycerides, said method comprising reacting an epoxidized triglyceride or alkyl esters thereof comprising one or more (esterified) epoxidized fatty acids comprising one or more oxirane rings of the formula:

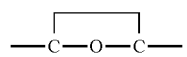

with a phosphorus-based acid hydroxide or ester of the formula $R_mP(O)_n\text{—}(OR')_q$ to open said oxirane ring and form one or both methylene groups of the formulas:

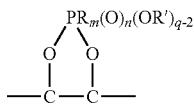 and 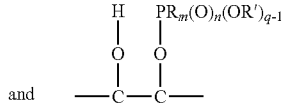

wherein m is 0, n is 0 or 1, q is 1, 2 or 3, and R and R' are independently selected from the group consisting of H, straight, branched or cyclic hydrocarbons and substituted hydrocarbons, and aryl groups; wherein if one R' is H then at least one of the other R' is not H; wherein said reacting an epoxidized triglyceride with said phosphorus-based acid hydroxide or ester is conducted in the presence of a catalyst effective for opening said oxirane ring, wherein said catalyst is selected from the group consisting of $TiO_2$, $ZrO_2$, and mixtures thereof.

2. The method of claim 1 wherein said methylene groups comprise said formula:

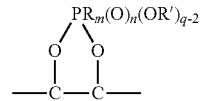

q is 2 or 3.

3. The method of claim 1 wherein said methylene groups comprise both of said formulas:

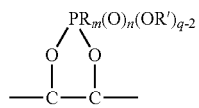 and 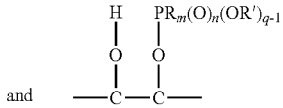

and q is 2 or 3.

4. The method of claim 1 wherein said methylene groups comprise said formula:

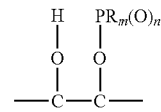

when q is 1.

5. The method of claim 1 wherein said phosphorus-containing triglyceride is of the formula:

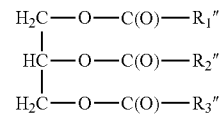

wherein $R_1"$, $R_2"$ and $R_3"$ are independently selected from C3 to C29 aliphatic fatty acid chains (residues), at least one of which comprising one or both of said methylene groups.

6. The method of claim 5 wherein one or more of said $R_1"$, $R_2"$ and $R_3"$ are independently selected from C7 to C21 aliphatic fatty acid residues.

7. The method of claim 5 wherein one or more of said $R_1''$, $R_2''$ and $R_3''$ are independently selected from C16 to C18 aliphatic fatty acid residues.

8. The method of claim 1 wherein said phosphorus-based acid hydroxide or ester is selected from the group consisting of phosphates (m=0, n=1 and q=3).

9. The method of claim 1 wherein said phosphorus-based acid hydroxide or ester comprises a phosphate.

10. The method of claim 9 wherein said triglyceride is selected from the group consisting of soybean, cottonseed, corn, olive, peanut, palm, sesame, sunflower, canola, castor, safflower, linseed, grapeseed, oiticia, tung, rice, crambe, rape, algae, and animal fat.

11. The method of claim 1 wherein said reacting an epoxidized triglyceride with said phosphorus-based acid hydroxide or ester is conducted in the absence of an added solvent.

12. The method of claim 1 further comprising producing said epoxidized triglyceride by reacting a triglyceride comprising one or more fatty acids having one or more sites of unsaturation —C=C—, with an epoxidation reagent to form said epoxidized triglyceride wherein at least one of said sites of unsaturation of said fatty acids is converted to said oxirane ring.

13. The method of claim 12 wherein said fatty acid having one or more sites of unsaturation —C=C— is selected from the group consisting of oleic acid, linoleic acid, linolenic acid, palmitoleic acid, erucic acid, 5-eicosenoic acid, 5-docosenoic acid, 5,13-docosadienoic acid, and petroselinic acid.

14. The method of claim 12 wherein said fatty acid having one or more sites of unsaturation —C=C— comprises oleic acid.

15. The method of claim 1 further comprising separating and recovering said phosphorus-containing triglyceride comprising said methylene groups of said formula:

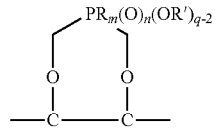

q is 2 or 3.

16. The method of claim 1 wherein said phosphorus-containing triglyceride comprising said methylene groups of said formula:

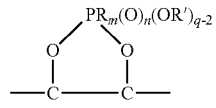

q is 2 or 3 are recovered in substantially pure form.

17. A cyclic triglyceride compound, said cyclic triglyceride comprising one or more phosphorus-containing fatty acid of the formula:

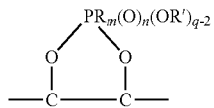 or 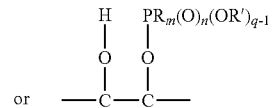

wherein in is 0, n is 0 or 1, q is 1, 2 or 3, and R and R' are independently selected from the group consisting of H, straight, branched or cyclic hydrocarbons and substituted hydrocarbons, and aryl groups; wherein if one R' is H then at least one of the other R' is not H.

18. The cyclic triglyceride derivative compound of claim 17 wherein said methylene groups comprise said formula:

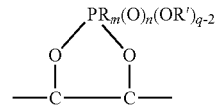

and q is 2 or 3.

19. The cyclic triglyceride compound of claim 18 in substantially pure form.

20. The cyclic triglyceride compound of claim 17 wherein said methylene groups comprise said formula:

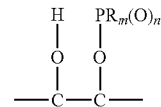

when q is 1.

21. The cyclic triglyceride compound of claim 20 in substantially pure form.

22. The cyclic triglyceride compound of claim 17 of the formula:

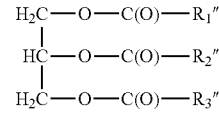

wherein $R_1''$, $R_2''$ and $R_3''$ are independently selected from C3 to C29 aliphatic fatty acid residues, at least one of which comprising one or more of said phosphorus-containing fatty acids.

23. The cyclic triglyceride compound of claim 22 wherein one or more of said $R_1''$, $R_2''$ and $R_3''$ are independently selected from C7 to C21 aliphatic fatty acid residues.

24. The cyclic triglyceride compound of claim 22 wherein one or more of said $R_1''$, $R_2''$ and $R_3''$ are independently selected from C16 to C18 aliphatic fatty acid residues.

25. The cyclic triglyceride compound of claim 17 wherein said m=0, n=1 and q=3, or m=1n=1 and q=2, or m=2, n=1 and q=1, or m=0, n=0 and q=3.

26. The cyclic triglyceride compound of claim 17 wherein said m=0, n=1 and q=3.

27. A composition comprising a base stock material of mineral, vegetable, animal or synthetic origin, or mixtures thereof, and a cyclic triglyceride compound, said triglyceride compound comprising one or more phosphorus-containing fatty acids of the formula:

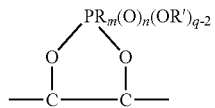 or 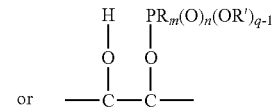

wherein m is 0, n is 0 or 1, q is 1, 2 or 3, and R and R' are independently selected from the group consisting of H, straight, branched or cyclic hydrocarbons and substituted hydrocarbons, and aryl groups; wherein if one R' is H then at least one of the other R' is not H.

28. The composition of claim 27 wherein said triglyceride compound comprises methylene groups of said formula:

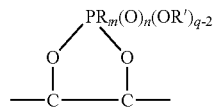

and q is 2 or 3.

29. The composition of claim 28 wherein said triglyceride compound is in substantially pure form.

30. The composition of claim 27 wherein said triglyceride compound comprises said methylene groups of said formula:

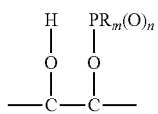

when q is 1.

31. The composition of claim 30 wherein said triglyceride compound is in substantially pure form.

32. The composition of claim 27 wherein said triglyceride compound is of the formula:

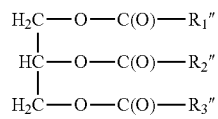

wherein $R_1''$, $R_2''$ and $R_3''$ are independently selected from C3 to C29 aliphatic fatty acid residues, at least one of which comprising one or more of said phosphorus-containing fatty acid.

33. The composition of claim 32 wherein one or more of said $R_1''$, $R_2''$ and $R_3''$ are independently selected from C7 to C21 aliphatic fatty acid residues.

34. The composition of claim 32 wherein one or more of said $R_1''$, $R_2''$ and $R_3''$ are independently selected from C16 to C18 aliphatic fatty acid residues.

35. The composition of claim 27 wherein said m=0, n=1 and q=3, or m=1, n=1 and q=2, or m=2, n=1 and q=1, or m=0, n=0 and q=3.

36. The composition of claim 27 wherein said m=0, n=1 and q=3.

* * * * *